US010251402B2

(12) United States Patent
Mafra-Neto et al.

(10) Patent No.: US 10,251,402 B2
(45) Date of Patent: Apr. 9, 2019

(54) METHODS AND COMPOSITIONS FOR CONTROLLING LEAF-CUTTING ANT POPULATIONS

(71) Applicant: ISCA Technologies, Inc., Riverside, CA (US)

(72) Inventors: Agenor Mafra-Neto, Riverside, CA (US); Rodrigo Oliveira Da Silva, Riverside, CA (US); Rafael Borges, Riverside, CA (US); Leyza Paloschi De Oliveira, Cacador (BR)

( * ) Notice: Subject to any disclaimer, the term of this patent is extended or adjusted under 35 U.S.C. 154(b) by 0 days.

(21) Appl. No.: 15/143,097

(22) Filed: Apr. 29, 2016

(65) Prior Publication Data

US 2016/0316764 A1 Nov. 3, 2016

Related U.S. Application Data

(60) Provisional application No. 62/155,842, filed on May 1, 2015.

(51) Int. Cl.
*A01N 65/16* (2009.01)
*A01N 61/02* (2006.01)
*A01N 37/40* (2006.01)

(52) U.S. Cl.
CPC .............. *A01N 65/16* (2013.01); *A01N 37/40* (2013.01)

(58) Field of Classification Search
CPC ................................ A01N 37/40; A01N 65/16
USPC ........................................................... 424/84
See application file for complete search history.

(56) References Cited

U.S. PATENT DOCUMENTS

2003/0194454 A1* 10/2003 Bessette ................. A01N 31/04 424/745
2014/0322339 A1* 10/2014 Folgarait .............. A01N 25/006 424/490

FOREIGN PATENT DOCUMENTS

WO WO 2012050857 A1 * 4/2012 ............. A01N 63/04

OTHER PUBLICATIONS

Dos Santos et al. "Plant-Derived Products for Leaf-Cutting Ants Control" Jan. 30, 2013. Retrieved from website: www.intechopen.com/books/insecticides-development-of-safe-and-more-effective-technologies/plant-derived-products-for-leaf-cutting-ants-control.
PCT/US2013/30276 International Search Report, dated Aug. 5, 2016. Authorized Officer Lee W. Young.

* cited by examiner

*Primary Examiner* — Carlos A Azpuru
*Assistant Examiner* — Courtney A Brown
(74) *Attorney, Agent, or Firm* — Benjamin Diederich

(57) ABSTRACT

Methods and compositions in which botanical oils, such as wintergreen oil, and/or isolated methyl salicylate are combined with an attractant matrix (pellets) and applied near a nest of leaf-cutting ants. These oils possess fungicidal and fungistatic properties that destroy and inhibit growth of the ant-cultivated fungus—the ant colony's sole food source—thereby promoting destruction of the colony. These oils are also highly attractive to the ants, exerting no repellent effects, encouraging transport of the fungicidal materials into the nest and ensuring that the fungal colonies come into contact with the materials and suffer mortality.

16 Claims, No Drawings

METHODS AND COMPOSITIONS FOR CONTROLLING LEAF-CUTTING ANT POPULATIONS

CROSS-REFERENCE TO RELATED APPLICATIONS

This application claims the benefit of U.S. Provisional Patent Application No. 62/155,842, filed on May 1, 2015, the teachings of which are expressly incorporated by reference.

STATEMENT RE: FEDERALLY SPONSORED RESEARCH/DEVELOPMENT

Not Applicable

BACKGROUND

Field of the Invention

The present invention relates to products, systems, and methods for controlling leaf cutter ants (LCA), significant pests of agriculture and forestry throughout the southern U.S., Central and South America. More specifically, this invention relates to methods and systems for 1) inducing foraging leaf cutter ants to orient to, collect, and transport back to their nests a fungicide-laced bait material, 2) inducing these ants to provide the material to the fungal gardens upon which the colony relies as its sole food source, and 3) producing mortality in or halting growth of the fungal colony, thereby depriving the ants of their only sustenance and causing all individuals therein to starve to death. All aspects of the invention will contribute to elimination of LCA colonies within the treated area, consequently reducing the damage caused by these insects to susceptible agricultural crops and forested land.

Background of the Invention

Leaf-cutting ants (LCA), a group which comprises approximately 40 different species of ants, range from the southern U.S. (Texas, Louisiana, and New Mexico) through Central America and in South America, as far south as Argentina, and are considered some of the most impactful herbivores of their ecosystem. In tropical forests, it is estimated that LCA of the genus *Atta* consume 12 to 17% of all leaves produced in the ecosystem, while grass-cutting ants have been found to significantly impact pasture growth, reducing this land's commercial value by up to 10% in Paraguay and Brazil. A single LCA nest may contain as many as 2 million individual insects, occupy 1 acre in space and extend up to 25 feet below ground, and displace 40,000 kg of soil during excavation. One study estimated that a single species (*Atta cephalotes* L.) was capable of executing a complete turnover of all soil in a Costa Rican rainforest over a period of 2 to 3 centuries. Through these activities, LCA have a profound effect on their environment, impacting microclimate, forest structure and regeneration.

The most northern-distributed member of the *Atta* genus, the Texas leaf-cutting ant (*Atta texana* Buckley), is currently found in 129 counties in the state of Texas and 13 parishes in Louisiana, and causes a significant degree of economic damage throughout this range. In Texas, LCA are pests of multiple fruit and nut crops, including peach, plum, blackberry, and citrus; cereal crops; and ornamental plants, as well as many key forestry species. Certain species of *Atta* are so voracious in their leaf-cutting activity that a single colony can completely defoliate entire citrus trees in a period of less than a day. Agricultural losses across Louisiana and Texas due to LCA activity typically hover around $5 million each year. While LCA usually prefer broad-leaved trees, they will target pines during the winter, when their preferred host plants are unavailable, and can cause significant damage to young pines when ant populations are high, particularly in recent plantings. This makes them a major pest of concern to reforestation programs. At heavily infested sites, LCA can damage pine seedlings to the point of death in only a few days, rendering natural tree reproduction impossible unless the ant population can be adequately controlled. The Texas leaf-cutter ant kills pine seedlings equivalent to an average area of 12,000 acres each year, resulting in an average of $2.3 million in costs for replanting and ant control. While creating their massive nests, these insects can also physically damage the stability of roads and farmland. Throughout LCA's range across North and South America—where the ants are pests of multiple commercial crops, such as coffee, banana, mango, cacao, citrus, and others—these insects are responsible for an approximate total of $1 billion in yearly losses.

Leaf cutter ants can travel 600 feet or farther from their nest in search of appropriate plant material, forming foraging trails along which the insects travel back and forth. Once a suitable plant is located, the ants attack en masse, sometimes in numbers large enough to strip an entire small or medium-sized tree in a single night. The ants cut fragments of leaves and carry them in their mandibles back to the entrance of the nest. The ants do not actually feed upon these leaves, but cut them into small pieces to provide a suitable food source for a symbiotic fungus which they cultivate within special chambers in the nest. Leaf cutter ants feed on certain parts of this fungus as their sole food source, both as larvae and adult insects. In order to tend this fungal garden, the ants not only provide plant material for nutrition, they also produce enzymes and amino acids to support the growth of the fungus, as well as substances that prevent the growth of competing fungi within the nest. The ants and the fungus are entirely dependent upon one another for survival. The ants provide a unique habitat in which the fungus can thrive, providing and maintaining an environment that is free of all potential competition, as well as any microorganism or pathogen that could do it harm, while the ants rely on the fungus as their only food source. Hence, the absence of one would soon result in the disappearance of the other.

Control of LCA has proved challenging, due to the protection provided to the colony by their massive and complex underground nests. The organobromine insecticide methyl bromide was successfully used against LCA for over half a century, but the U.S. Environmental Protection Agency (EPA) discontinued its use against these ants in 2005 (most other uses have also been phased out) due to its potential risk of ozone depletion. Plants susceptible to attack by LCA can be protected for short periods through application of contact insecticides, including carbaryl or permethrin, but these treatments must be repeated frequently in order to maintain this protective effect, and make no impact on the survival of LCA colonies in the area. Furthermore, because ants feed only on the fungus cultivated within their nests, conventional ant baits typically do not work as effectively for LCA as for other species of ant pests, such as fire ants. The only ant bait currently available for LCA control is a product called Amdro® Ant Block, a formulation of the insecticide, hydramethylnon, which was originally designed for fire ants. This product has been identified as relatively safe, and can be applied to lawns, ornamental gardens, roadsides, etc. However, this product has several shortcomings. It has a relatively brief shelf life, and so cannot be stored for long periods; and while it does suppress LCA activity, it does not consistently eradicate the nest. In roughly half of cases, LCA activity rebounds 4 to 6 months after application, though typically not to pre-treatment levels. Perhaps most limiting, this product cannot be applied on agricultural land. The same is true for an injection method of fipronil, which has been approved for forestry management of LCA, but is currently not permitted for other applications.

There is an urgent need to develop new ways to control these ants, to address the economic threat they pose, but also the preservation of the environment, to reduce residual effects caused by the indiscriminate use of chemicals. A highly promising alternative to conventional chemical insecticide-based management is the use of natural products from plants potentially toxic to the fungus and/or the ants. Attempts have been made to create bait formulations using organic plant materials (dehydrated citrus pulp, corn, eucalyptus leaves, cassava flour, wheat flour, soy bran, molasses) coupled with sugar-based attractants (glucose, fructose, or sucrose), with the purpose of causing mortality of the specific caste of ants responsible for the maintenance and rearing of the symbiotic fungus. Because the ants are so entirely dependent on their fungal colonies for sustenance, and because the responsibility for their care is placed only on a particular caste of individuals within the nest, the elimination of this caste is intended to trigger a deadly chain of events, eventually resulting in the annihilation of the colony. As the ants responsible for the maintenance of the colony begin to die off, the health of the symbiotic fungus begins to deteriorate, since there are no other individuals within the colony to replace the care workers who have been lost. Eventually, this deterioration progresses to such a degree that the fungus becomes unsuitable for consumption by the ants, and all members of the colony, including the queen, starve to death.

The present invention aims to achieve this end through a more direct approach to LCA control, targeting the fungus itself, rather than the ants responsible for caring for it. This invention consists of a bait pellet formulation designed to attract LCAs and induce them to pick up the pellet and carry it back to their nests. However, in place of an insecticidal agent intended to produce mortality in the ants, our bait formulation will be impregnated with a blend of natural botanical fungicides (wintergreen oil, methyl salicylate, and their constituents, concentrations ranging from 0.1 to 75%) that are highly attractive to the ants, exerting no repellent effects—a critical advantage over many insecticides, as any level of repellency could prevent introduction of these fungicides into the nest. Once these pellets are carried into the nest, directly to the chambers in which LCA fungal gardens are cultivated, the incorporated fungicidal and fungistatic agents will infect the fungal garden, halting its growth and eventually resulting in its death. Without the fungus to rely upon as a food source, the ant colony will quickly follow.

Results of testing with these fungicidal and fungistatic materials have demonstrated that exposure to wintergreen oil produced total annihilation of the fungus, and both wintergreen oil and methyl salicylate can suppress 100% of fungal growth under laboratory conditions. Ongoing field tests of the invention have also produced encouraging results: bait pellets impregnated with wintergreen oil suppressed activity of LCA colonies in Brazil to zero within an interval of 42 to 63 days after application. In addition to this excellent degree of efficacy against the target insects, this invention presents multiple advantages over current LCA control strategies. This bait formulation does not contain any amount of conventional chemical insecticide, relying instead on a blend of botanical oils, which, in spite of their fungicidal activity, have no negative impacts on people, on non-target species (with the exception of other fungi), or on the environment. Wintergreen oil has actually been used as an herbal pain remedy throughout North American history. Application of this invention will help to reduce the impact of LCA cutting and nest building activity, protecting the value of susceptible agricultural crops and forestry species throughout its geographic range, without resorting to additional inputs of potentially harmful conventional pesticides.

BRIEF SUMMARY

In accordance with one embodiment of the present disclosure, there is contemplated a method of controlling a leaf-cutting ant population in a region. The method involves administering a composition containing at least one fungicide to the region containing leaf-cutting ants. In particular, the composition may be designed so as to not repel the leaf-cutting ants, and may further be designed to actually attract the leaf-cutting ants to the composition. Furthermore, the composition may be formulated such that it does not harmfully affect non-target organisms or the environment within the region.

In that regard, the fungicide in the composition may be a wintergreen oil extracted from leaves of a plant within the *Gaultheria* genus, methyl salicylate, or a combination of a wintergreen oil extracted from leaves of a plant within the *Gaultheria* genus and methyl salicylate.

The composition may further include a carrier bait pellet to distribute the fungicides. The pellet may be formulated from a combination of citrus pulp, soybean oil, wheat flour, and carboxymethyl cellulose. In one embodiment, the carrier bait pellet may have the following formula:

| | |
|---|---|
| citrus pulp | 84% by weight; |
| soybean oil | 8% by weight; |
| wheat flour | 7.5% by weight; and |
| carboxymethyl cellulose | 0.5% by weight. |

In certain embodiments, the fungicide may be present in the composition in a range between about 0.1% by weight to about 75% by weight, and more particularly may be present in the composition in a range between about 1% by weight to about 10% by weight, and even more particularly may be present in the composition in an amount of about 5% by weight.

Furthermore, the composition may be administered to the region in certain embodiments in a range from about 10 grams of composition per square meter to about 50 grams of composition per square meter, and more particularly may be administered to the region in an amount of about 20 grams of composition per square meter. Additionally, the composition may be administered on or near known foraging trails of the leaf-cutting ant population.

Alternatively to the specific carrier pellet described above, in certain embodiments, the composition may include various types of carriers, such as, but not limited to, inert dry carrier materials, liquid carrier materials, food bases, pellets, pastes, emulsions, fog vapors, and/or sprayable monolithic lures such as SPLAT described more fully below.

Another embodiment of the present disclosure includes compositions for controlling a leaf-cutting ant population, wherein the composition includes at least one fungicide selected from the group consisting of wintergreen oil extracted from leaves of a plant within the *Gaultheria* genus, methyl salicylate, and combinations thereof. The composition may further include at least one leaf-cutting ant attractant. These attractants may be, but are not limited to, fruit pulps, sugars, and combinations thereof.

The fungicide of the composition may be integrated into a carrier bait pellet. The carrier bait pellet may be made from a combination of citrus pulp, soybean oil, wheat flour, and carboxymethyl cellulose. In one particular embodiment, the carrier bait pellet has the following formula:

| | |
|---|---|
| citrus pulp | 84% by weight; |
| soybean oil | 8% by weight; |
| wheat flour | 7.5% by weight; and |
| carboxymethyl cellulose | 0.5% by weight. |

The may alternatively utilize a carrier such as but not limited to, inert dry carrier materials, liquid carrier materials, food bases, pellets, pastes, emulsions, fog vapors, and/or sprayable monolithic lures, such as SPLAT.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The present disclosure envisions a plant-based fungicidal bait designed to annihilate entire colonies of leaf cutter ants (LCA) by infecting the fungal gardens they cultivate within their nests, comprised of *Leucoagaricus gongylophoros* Singer (Möller), with compounds toxic to the fungi, thereby halting their growth and eventually resulting in their death. Because LCA rely upon these fungal gardens as their only source of food, the death of the fungus resulting from exposure to the toxic bait inevitably results in the death of all ants within the colony due to starvation. This invention is a novel approach to LCA control compared to other ant baits, which have typically targeted the ants themselves rather than the mutualistic fungus.

These ant baits have typically consisted of an insecticidal active ingredient (AI) incorporated into a substrate composed of dehydrated citrus pulp. Orange pulp has proven to the most effective, although a number other organic materials have also been used (corn, eucalyptus leaves, cassava flour, soy bran, wheat flour, molasses, and bagasse). These types of baits possess a number of attributes that would seem to make this material an ideal nutritive source for the ants' fungal gardens: slight acidity, high carbohydrate content, presence of nitrogen and a wide array of vitamins and microelements. These characteristics encourage the ants to pick up particles of this substrate, usually applied as pellets or granules, and carry them back into their nests in the same way they forage for and transport leaf fragments. This gives the bait approach an enormous advantage over cover sprays of conventional insecticides: these chemicals typically do not penetrate far enough into the nest, which can consist of hundreds of chambers and galleries, to kill any significant portion of either the ant or the fungal colony. By "piggy-backing" the ants themselves, bait-type control strategies ensure that the lure/toxicant formulation reaches the location where it can inflict the greatest impact on the largest number of insects. The ants' response to these baits can be strengthened by the addition of certain sugars. In particular, researchers have found that sucrose, glucose, and fructose were the most attractive to leaf cutter species, *Atta cephalotes* and *Acromyrmex octospinosus*.

The present disclosure adopts the organic bait approach and its advantages, but rather than incorporating an insecticidal agent to kill the ants, the envisioned product is impregnated with a botanical oil that is toxic to the symbiotic fungus itself, but is attractive to foraging ants, exerting no negative impacts on the target insects—either in terms of insecticidal activity or repellency—ensuring that the fungicidal and fungistatic oils are successfully introduced into the LCA fungal colony. This may be expected to provide a more direct and faster acting method of LCA control, as it shortens the mortality cascade effect. With a typical insecticidal ant bait, the chain of events leading to the annihilation of the LCA colony is as follows: The ants encounter the insecticide-laced bait, identify it as a potential food source for the fungal colony, and carry it back to the nest. There, the caste of ants who are responsible for rearing, feeding, and maintenance of the fungal colonies eventually come into contact with the bait material, and suffer mortality as a result. Because different groups of ants are dedicated to different tasks within the nest, the loss of this group of ants will deprive the fungal gardens of their only caretakers, causing their health to degrade over time. As the fungus sickens and begins to die off, it eventually becomes unsuitable for consumption by the ants, who in their turn begin to starve to death. By shortening this chain of events, targeting the fungus directly rather than waiting for it to die in the absence of the ants who tend to it, the present compositions may shorten the interval between the application of the baits and the annihilation of the colony.

The compositions discussed herein can be applied in a similar manner to traditional ant baits; as dry pellets scattered on the ground near LCA nests, along the trails used by the ants to forage for leaf material to feed to their fungal symbionts. The pellets are prepared according to the procedure described by Oliveira (2006), with the following composition: 84% citrus pulp, 8% soybean oil, 7.5% wheat flour, and 0.5% carboxymethyl cellulose (CMC). Beyond that, a highly advantageous AI is added to these pellets, at a concentration range between 0.1 and 75%: wintergreen oil (experimental formulations have contained concentrations between 5 and 10%) with, or without, isolated methyl salicylate.

Wintergreen oil is derived from a group of plants of the genus *Gaultheria* (multiple common names, including American mountain tea, boxberry, creeping wintergreen, spice berry, and hillberry, among others). The term "wintergreen" is a somewhat antiquated reference to the ability of these plants to sustain photosynthetic activity throughout the winter; the term "evergreen" is now more commonly used to describe this characteristic. Wintergreen oil is derived from *Gaultheria* plants by steam distillation of their leaves, following maceration in warm water. This process produces an enzymatic action by a glycoside within the leaves, yielding the main constituent of wintergreen oil, methyl salicylate—a critical component of the invention described herein. The oil itself is a pale yellow or pinkish fluid that is strongly aromatic, with a sweet woody odor. The components of wintergreen oil are: methyl salicylate (~98%), α-pinene, myrcene, delta-3-carene, limonene, 3,7-guaiadiene, and delta-cadinene, which gives wintergreen plants a distinctive “medicinal” smell whenever bruised.

Recent research has demonstrated that wintergreen oil and its main constituent, methyl salicylate, possess fungistatic and fungicidal properties, which if incorporated into bait formulations like those described previously, will cause the fungus to break down and consequently lead to the annihilation of the entire LCA colony. These compounds do not cause either repellency or mortality to the worker caste of ants, and therefore do not interfere with the attractancy of the bait, ensuring that the ants readily transport the fungicidal material into the nest, introducing it into their fungal gardens. An ant bait that relies upon wintergreen oil rather than an insecticide, as standard baits include, possesses a strong advantage in terms of safety and environmental sustainability. Wintergreen oil is a naturally occurring botanical substance with no known impacts on people, on other non-target organisms, or on the environment; in fact, wintergreen plants are often used for medicinal purposes. Native Americans brewed a tea from the leaves to alleviate rheumatic symptoms, headache, fever, sore throat, and various other aches and pains. Methyl salicylate is currently a widely used component of topical analgesics.

During the development of the compositions discussed herein, laboratory trials involving the exposure of the LCA symbiotic fungus, *Leucoagaricus gongylophorus*, to wintergreen oil produced excellent results in terms of fungal mortality and suppression of fungal colony growth. When inoculations of the fungus—isolated from a nest of *Atta sexdens rubropilosa*—were exposed to 50 mL wells containing various botanical oils and extracts (compared to controls, in which the well was left empty) for a period of 21 days, both wintergreen oil and methyl salicylate suppressed fungal growth by 100%, as measured by the rate of growth of fungal mycelia toward the well, compared to that seen in the unexposed controls, as can be seen by the results in Table 1.

TABLE 1

Fungistatic inhibition activity of oils against the symbiotic fungus *Leucoagaricus gongylophorus*.

| Compound | Inhibition (%) |
|---|---|
| Sesame Oil | 14.4 |
| Thyme Oil | 100 |
| Cinnamom Leaf Oil | 85.7 |
| Rosemary Oil | 100 |
| Peppermint Oil | 100 |
| Wintergreen oil | 100 |
| Clove Oil | 97.1 |
| Methyl Salicylate | 100 |

A similar lab trial was designed and performed to evaluate the fungicidal capacities of these botanical oils in addition to their fungistatic properties against *L. gongylophorus*. For this test, the plant oils were incorporated directly into the fungal growth medium at different concentrations (0.1, 1, and 5%). The growth of the fungus on this medium was evaluated after a 30-day incubation period, based on the quantity and density of the mycelium, according to the following pattern. Growth was characterized by the following measure: 5+ indicated growth identical to the control treatment (medium alone, with no plant oil treatment), or 100% growth; 4+ indicated growth equivalent to 80% of the control treatment growth; 3+ indicated 60%; 2+ indicated 40%; 1+ indicated 20%; and 0 indicated total elimination of the fungal colony. Wintergreen oil successfully eliminated all fungal colonies at all concentrations, while its main constituent, methyl salicylate, achieved 100% fungal mortality at the two highest concentrations, 1% and 5%, as can be seen by the results in Table 2.

TABLE 2

Fungicidal activity of oils against the symbiotic fungus *Leucoagaricus gongylophorus*, as expressed by the median of five replicates.

| | Concentration (%) | | |
|---|---|---|---|
| | 0.1 | 1 | 5 |
| Compound | Growth Evaluation | | |
| Sesame Oil | 5+ | 5+ | 5+ |
| Thyme Oil | 2+ | 5+ | 5+ |
| Cinnamom Leaf Oil | 1+ | 1+ | 1+ |
| Rosemary Oil | 1+ | 0 | 0 |
| Peppermint Oil | 1+ | 1+ | 0 |
| Wintergreen oil | 0 | 0 | 0 |
| Clove Oil | 1+ | 0 | 0 |
| Methyl Salicylate | 3+ | 0 | 0 |

In addition to these lab trials with the botanical AIs of the present invention, field trials have also been conducted in Brazil, using the following pellet formulation, prepared according to the procedure described above: 84% citrus pulp, 8% soybean oil, 7.5% wheat flour, and 0.5% carboxymethyl cellulose (CMC), in a concentration of 4%. Wintergreen oil was also added to this formulation, at an experimental dosage of 5 to 10%. After this mixture was heated and processed in an adapted small scale grinder, yielding pellets of 2 to 5 mm in length, the baits were cooled, packed, and stored until transport to the field test sites, which consisted of individual *A. sexdens rubropilosa* nests (minimum area: 2 m2) identified in the city of Amparo, Sao Paulo, Brazil. Four colonies were selected: three to receive treatment with the wintergreen oil pellets, applied at a rate of 20 g of pellets per m2, and one to be left untreated, to serve as a control. Twenty-four hours after application, the sites were observed to evaluate the quantity of pellet formulation still remaining on the ground (not taken up by the ants). Evaluations of ant activity at each of the colonies were performed 1, 7, 14, 28, 35, 42 and 63 days after application, as shown in Table 3.

Ants were observed to have taken up nearly half of the applied pellets (48% on average) 24 hours after application. The wintergreen oil-impregnated bait pellets achieved complete suppression of LCA activity in one of the treated nests within 42 days after application; activity was suppressed to zero at the second nest as well on the following sampling date, Day 63 following application. Taking all three replicates into account, the wintergreen oil pellet formulation achieved 96.6% control of the LCA population at the treated colonies 63 days after application. As can be seen, this composition is capable of competing effectively with other ant baits, with the added advantage of being an entirely non-toxic, environmentally friendly LCA control option.

TABLE 3

Suppression of *Atta sexdens rubropilosa* colony activity following application of wintergreen oil ant baits.

| Time | % OF ANTS/COLONY ACTIVITY | | | |
|---|---|---|---|---|
| | Colony 1 (15 $m^2$) | Colony 2 (15 $m^2$) | Colony 3 (25 $m^2$) | Control |
| Day 1 | 100 | 100 | 100 | 100 |
| Day 7 | 100 | 100 | 100 | 100 |
| Day 14 | 100 | 100 | 100 | 100 |
| Day 28 | 80 | 85 | 85 | 100 |
| Day 35 | 20 | 30 | 60 | 100 |
| Day 42 | 0 | 10 | 20 | 100 |
| Day 63 | 0 | 0 | 10 | 100 |

During a second field trial in Caçador, Santa Catarina, targeting LCA of an *Acromyrmex* sp., the same wintergreen oil pellet formulation was applied at a rate of 20 g per colony. Eight colonies were selected for this trial, four receiving treatment with the wintergreen oil pellets, and the remaining half serving as a control (average area of the colonies was 0.15 m2). Twenty-four hours after application, the sites were observed to evaluate the quantity of pellet formulation still remaining on the ground (not taken up by the ants). Evaluations of ant activity at each of the colonies were performed 1, 7, 14, 28, 35 and 42 days after application. The results of this test showed, as can be seen in Table 4, that the wintergreen oil pellets suppressed colony activity by 96.6% in 35 days compared to untreated control—within the interval currently delivered by insecticidal ant baits (4-6 weeks)—and achieved complete control (100% suppression of activity) after 42 days.

TABLE 4

Suppression of *Acromyrmex* sp. colony activity following application of wintergreen oil ant baits.

| Time | % OF ANTS/COLONY ACTIVITY | | | | |
|---|---|---|---|---|---|
| | Colony 1 (0.10 $m^2$) | Colony 2 (0.12 $m^2$) | Colony 3 (0.23 $m^2$) | Colony 4 (0.33 $m^2$) | Control |
| Day 1 | 100 | 100 | 100 | 100 | 100 |
| Day 7 | 60 | 70 | 40 | 80 | 100 |
| Day 14 | 0 | 30 | 20 | 50 | 100 |
| Day 28 | 0 | 10 | 0 | 40 | 100 |
| Day 35 | 0 | 0 | 0 | 10 | 100 |
| Day 42 | 0 | 0 | 0 | 0 | 100 |
| Day 63 | 0 | 0 | 0 | 0 | 100 |

In addition to pellet formulations like that used in the field trials described above, wintergreen oil, methyl-salicylate, and its constituents are amenable to inclusion in many other forms of LCA control, including an inert dry carrier material, liquid carrier material, food base, pellets, paste, emulsions, or "fog" vapor. One particularly promising alternative embodiment, which has proven an effective delivery mechanism for multiple classes of insect attractants, is the biologically inert controlled-release matrix, SPLAT® (Specialized Pheromone and Lure Application Technology) described in U.S. Pat. No. 7,887,828, the entirety of which is incorporated by reference herein. This matrix is comprised entirely of food-safe, organic inert ingredients, adheres quickly and effectively to a wide variety of substrates including plant bark and foliage, and has demonstrated a consistent ability to release a broad range of attractants, repellents, phagostimulants, and other behavior modifying chemicals (also known as semiochemicals) at biologically active release rates, enabling season-long control for many insect pests.

SPLAT formulations belong to a "matrix-type" or "monolithic" category of controlled-release devices. These monolithic dispensers are defined as devices in which the AI is dispersed or dissolved in a polymer matrix. Release of the AI from a monolithic device occurs by diffusion and can be described macroscopically by Fick's Law, which states that the movement of a molecule by diffusion is directly proportional to the concentration of that molecule in a system. Microscopically, if one follows the movement of a molecule of an active agent through a matrix, this molecule begins its journey in one of two ways. If it is dispersed in the matrix, it begins its journey by dissociating from other molecules in its crystal cell and solubilizing into the polymer phase. If it is dissolved in the matrix, then this step is bypassed. The molecule then diffuses through amorphous regions in the matrix that comprise the free volume of the system. The molecule can move through the matrix in one of two ways. If it is very small compared to the size of the amorphous spaces in the matrix, then it will diffuse through the matrix by moving from one such space to another. If it is very large compared to the size of those spaces, then segments of the polymer comprising the matrix will have to be rearranged for diffusion of the active agent molecule to occur. Crystalline regions in the matrix are virtually impermeable to molecules of the active agent. Upon reaching the surface of the matrix, it will be released into the environment. A series of factors influence the rate of release of an active agent from a monolithic device and include properties of the matrix material as well as properties of the active agent. The temperature of the matrix influences release of the active agent; at higher temperatures the free volume is increased, and diffusion occurs faster. At lower temperatures, the free volume is decreased, and diffusion is slower. The thermal history of a polymer can also increase or decrease the free volume of the system and lead to changes in the diffusional rate of an active agent. The property of the AI having the greatest influence on its release rate is its molecular weight. Generally, larger molecules take more time to make their way through the free space of a matrix. The partition coefficient of the active agent between the matrix and the environment can also influence the release rate of that agent. If the agent readily partitions to the environment, then its rate of release will be diffusion-controlled and first order. If, however, partitioning of the active agent to the environment is relatively slow, then its partition coefficient will determine its release rate from the matrix, and the device will exhibit zero-order release kinetics. The partitioning of the AI to the environment is a function of its solubility in the matrix; compounds more soluble in the matrix partition to the environment more slowly. SPLAT emulsions in a field environment exhibit diffusion-controlled release. The surface area of the device also influences its release rate. SPLAT dispensers with larger surface areas release AIs at faster rates.

SPLAT formulations' performance in the field can also be adjusted by changes in its composition, both in the emulsion matrix itself and in the blend and dosage of the AIs incorporated. The biodegradable wax carrier consists of a wax selected from the group including beeswax, lanolin, shellac wax, carnauba wax, fruit wax (such as bayberry or sugar cane wax), candelilla wax, hydrocarbon-based waxes (paraffin wax), microcrystalline, vegetable-based waxes (soy wax), or combinations thereof. These wax components may be present in the formulation in an amount ranging from about 10% to 90%, by weight of the total formulation. Yet other components which may be included in the formulation to improve field persistence and fine-tune AI release rates include humectants, preservatives, or antimicrobial agents, thickeners, antimicrobial agents, antioxidants, emulsifiers, film-forming polymers, sunlight stabilizers and mixtures thereof, depending on the requirements of the pest or the field environment. Additives which retard or slow the volatilization of the active mixture are preferred. Humectants may include polyols, sugars and glycols and more preferred humectants include glycerol, honey and sorbitol. Antioxidants which reduce polymerization of phenyl acetaldehyde are preferred and these may include butylated hydroxytoluene (BHT), butylated hydroxyanisole (BHA) and D/L alpha tocopherol (Vitamin Film forming polymers include gum rosin, latex, polyvinyl pyrrolidone, polyvinyl alcohol, polyvinylchloride, polyethylene, polyvinyl acetate and mixtures thereof. Suitable thickeners include xanthan gum, hydroxycellulose gums, carageenan, tragacanth, locust bean gum and guar. Examples of suitable sunlight stabilisers are titanium oxide and Zinc oxide. Additional optional additives include, shellac, methyl methacrylate, and mixtures thereof. In terms of AI blend and loading rate, the concentration range of the most critical AIs (wintergreen oil, methyl salicylate, and their constituents) is widely adjustable, from 0.1 to 75%. LCA attractant composition may be further formulated with a variety of optional components or adjuvants, including but not limited to other plant volatiles, feeding stimulants such as citrus, apple, mango or other fruit pulps, and sugars like sucrose, fructose, and glucose, which have previously been identified as effective against *Atta* species.

Application Methods:

The composition described herein, when deployed in the form of bait pellets, can be applied in a similar manner to other ant baits. Once a nest of LCA is located and determined to be active, wintergreen oil pellets should be applied to the ground along the foraging tracks used by the worker ants to travel to and from the nest, transporting plant material to the fungal gardens sheltered within. The exact application rate for these pellets may be variable based on the species of ant, the size of the colony, and other factors. However, the pellet application rate of 20 g per m2 has shown strong results in field trials.

These wintergreen oil and methyl salicylate AIs could also be applied by multiple other methods, in vapor or liquid form. A SPLAT formulation (or other liquid or thin paste formulation) containing wintergreen oil, methyl salicylate, and its constituents can be sprayed into the entrance of the LCA nest, or loaded into a pressurized injection system to be pumped in directly, contaminating the entire nest, including the chambers in which the fungal gardens are cultivated. A vaporized formulation of the same AIs could be introduced into the nest using a fogging device or a thermo-nebulization system, a common technique in Brazil, in which mineral oil is used as an inert aerosol vapor carrier. In one embodiment, the formulation could be applied using a commercially available dusting device or aerosol applicator. Examples of such applicators include compression sprayers, such as pump type sprayers with pistons or plungers, motorized dusters, bulb dusters, thermo-nebulizers, or fogging machines. The tube of the equipment is inserted into a ventilation hole or entrance of an ant nest and the plunger is pumped several times to produce an air stream that blows the formulation and carrier into the nest chambers containing the fungal colony. The amount of product required to be applied in any of these scenarios to achieve effective LCA control may be determined by the size of the nest and intensity of ant activity in the affected area.

The above description is given by way of example, and not limitation. Given the above disclosure, one skilled in the art could devise variations that are within the scope and spirit of the invention disclosed herein, including various ways of delivering the composition to the region, different dosing amounts of the composition, and utilizing different carrier agents. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of controlling a leaf-cutting ant population in a region, the method comprising administering a composition to the region, said composition comprising:

at least one fungicide selected from the group consisting of wintergreen oil extracted from the leaves of a plant within the *Gaultheria* genus, methyl salycylate, and combinations thereof; and a carrier bait pellet in which the at least one fungicide is integrated, wherein the carrier bait pellet comprises:

| | |
|---|---|
| citrus pulp | 84% by weight; |
| soybean oil | 8% by weight; |
| wheat flour | 7.5% by weight; |
| carboxymethyl cellulose | 0.5% by weight. |

2. The method of claim 1, wherein the composition does not repel leaf-cutting ants.

3. The method of claim 1, wherein the composition attracts leaf-cutting ants.

4. The method of claim 1, wherein the composition does not harmfully affect non-target organisms or the environment within the region.

5. The method of claim 1, wherein the at least one fungicide is present in the composition in a range between about 0.1% by weight to about 75% by weight.

6. The method of claim 5, wherein the at least one fungicide is present in the composition in a range between about 1% by weight to about 10% by weight.

7. The method of claim 6, wherein the at least one fungicide is present in the composition in an amount of about 5% by weight.

8. The method of claim 1, wherein the composition is administered to the region in a range from about 10 grams of composition per square meter to about 50 grams of composition per square meter.

9. The method of claim 8, wherein the composition is administered to the region in an amount of about 20 grams of composition per square meter.

10. The method of claim 1, wherein the composition is administered on or near known foraging trails of the leaf-cutting ant population.

11. A composition for controlling a leaf-cutting ant population comprising:

at least one fungicide selected from the group consisting of wintergreen oil extracted from the leaves of a plant within the *Gaultheria* genus, methyl salycylate, and combinations thereof; and a carrier bait pellet in which the at least one fungicide is integrated, wherein the carrier bait pellet comprises:

| | |
|---|---|
| citrus pulp | 84% by weight; |
| soybean oil | 8% by weight; |
| wheat flour | 7.5% by weight; |
| carboxymethyl cellulose | 0.5% by weight. |

12. The composition of claim 11, further comprising a leaf-cutting ant attractant.

13. The composition of claim 12, wherein the attractant is selected from the group consisting of fruit pulps, sugars, and combinations thereof.

14. The composition of claim 11, wherein the at least one fungicide is present in the composition in a range between about 0.1% by weight to about 75% by weight.

15. The composition of claim 14, wherein the at least one fungicide is present in the composition in a range between about 1% by weight to about 10% by weight.

16. The composition of claim 15, wherein the at least one fungicide is present in the composition in an amount of about 5% by weight.

* * * * *